(12) United States Patent
Bae

(10) Patent No.: US 11,784,608 B2
(45) Date of Patent: Oct. 10, 2023

(54) DEVICE AND METHOD WITH POWER CONTROL

(71) Applicant: Samsung Electronics Co., Ltd., Suwon-si (KR)

(72) Inventor: Chisung Bae, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 17/506,878

(22) Filed: Oct. 21, 2021

(65) Prior Publication Data

US 2022/0045513 A1    Feb. 10, 2022

Related U.S. Application Data

(63) Continuation of application No. 16/663,840, filed on Oct. 25, 2019.

(Continued)

(30) Foreign Application Priority Data

Feb. 26, 2019    (KR) .................. 10-2019-0022751

(51) Int. Cl.
| | |
|---|---|
| H02S 40/32 | (2014.01) |
| H02S 40/38 | (2014.01) |
| H02J 3/38 | (2006.01) |
| H02J 7/34 | (2006.01) |
| H02S 50/10 | (2014.01) |
| H02J 50/30 | (2016.01) |
| H02J 7/35 | (2006.01) |
| A61B 5/00 | (2006.01) |

(52) U.S. Cl.
CPC ............. *H02S 50/10* (2014.12); *H02J 3/38* (2013.01); *H02J 3/388* (2020.01); *H02J 7/35* (2013.01); *H02J 50/30* (2016.02); *H02S 40/32* (2014.12); *H02S 40/38* (2014.12); *A61B 5/6847* (2013.01); *H02J 7/345* (2013.01)

(58) Field of Classification Search
CPC .. H02J 3/385; H02J 50/30; H02J 3/388; H02J 3/38; H02J 7/35; H02J 7/345; H02S 40/32; H02S 40/38; H02S 50/10; A61B 5/6847
USPC ........................................................ 307/52
See application file for complete search history.

(56) References Cited

U.S. PATENT DOCUMENTS

| | | | |
|---|---|---|---|
| 8,200,373 B2 | 6/2012 | Stiles, Jr. et al. | |
| 8,442,698 B2 | 5/2013 | Fahimi et al. | |
| (Continued) | | | |

FOREIGN PATENT DOCUMENTS

| | | |
|---|---|---|
| JP | 5944452 B2 | 7/2016 |
| KR | 10-2017-0075146 A | 7/2017 |
| (Continued) | | |

*Primary Examiner* — Michael R. Fin
(74) *Attorney, Agent, or Firm* — NSIP Law

(57) ABSTRACT

A microelectronic device includes: a photovoltaic module configured to convert a light energy into an electric energy; a converter configured to convert a voltage output from the photovoltaic module into a predetermined voltage; a capacitor configured to store an electric energy transferred from the converter; and a controller configured to predict an available current of a next time slot based on the electric energy stored in the capacitor, and determine a consumed current of a load system of the next time slot based on the predicted available current.

19 Claims, 10 Drawing Sheets

Related U.S. Application Data

(60) Provisional application No. 62/791,984, filed on Jan. 14, 2019.

(56) References Cited

U.S. PATENT DOCUMENTS

| | | |
|---|---|---|
| 9,166,405 B2 | 10/2015 | Brandt et al. |
| 9,722,420 B2 | 8/2017 | Teggatz et al. |
| 9,948,233 B2 | 4/2018 | Adest et al. |
| 9,991,715 B1 | 6/2018 | Huang et al. |
| 2008/0029153 A1 | 2/2008 | Margalit |
| 2011/0006742 A1 | 1/2011 | Teggatz et al. |
| 2012/0081088 A1 | 4/2012 | Park |
| 2017/0133938 A1 | 5/2017 | Tiefnig |
| 2017/0201099 A1 | 7/2017 | Savanth et al. |
| 2017/0324148 A1 | 11/2017 | Stevenson et al. |
| 2019/0190400 A1* | 6/2019 | Vanderzaden ...... H02M 7/4807 |
| 2020/0110614 A1* | 4/2020 | Ma ............................ G06F 1/26 |

FOREIGN PATENT DOCUMENTS

| | | |
|---|---|---|
| KR | 10-2017-0086783 A | 7/2017 |
| WO | WO 2014/169295 A1 | 10/2014 |

\* cited by examiner

DEVICE AND METHOD WITH POWER CONTROL

CROSS-REFERENCE TO RELATED APPLICATIONS

This application is a continuation of U.S. patent application Ser. No. 16/663,840 filed on Oct. 25, 2019, which claims the benefit under 35 U.S.C. § 119(e) of U.S. Provisional Application No. 62/791,984 filed on Jan. 14, 2019 in the U.S. Patent and Trademark Office, and claims the benefit under 35 U.S.C. § 119(a) of Korean Patent Application No. 10-2019-0022751 filed on Feb. 26, 2019 in the Korean Intellectual Property Office, the entire disclosures of which are incorporated herein by reference for all purposes.

BACKGROUND

1. Field

The following description relates to a device and method with power control.

2. Description of Related Art

Wireless power transmission technology may be used in various fields. For example, the wireless power transmission technology may be applied to in-vivo medical devices to provide various forms of medical services. However, when a device is manufactured in a small size for in-vivo insertion, a wireless power transmission efficiency may be degraded and a stable power supply may be difficult.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a microelectronic device includes: a photovoltaic module configured to convert a light energy into an electric energy; a converter configured to convert a voltage output from the photovoltaic module into a predetermined voltage; a capacitor configured to store an electric energy transferred from the converter; and a controller configured to predict an available current of a next time slot based on the electric energy stored in the capacitor, and determine a consumed current of a load system of the next time slot based on the predicted available current.

The controller may be configured to predict the available current of the next time slot based on any one or any combination of any two or more of: a determined change in an amount of electrical charge stored in the capacitor from a previous time slot to a current time slot; a determined difference between the amount of electrical charge stored in the capacitor in the current time slot and a target amount of electrical charge to be stored in the capacitor; and a determined change in an amount of output current of the converter from the previous time slot to the current time slot.

The controller may be configured to predict the available current of the next time slot to be greater than a predicted available current of the current time slot, in response to an increase in a degree to which the amount of electrical charge stored in the capacitor in the current time slot is greater than the amount of electrical charge stored in the capacitor in the previous time slot.

The controller may be configured to predict the available current of the next time slot to be greater than a predicted available current of the current time slot, in response to an increase in a degree to which the amount of electrical charge stored in the capacitor in the current time slot is greater than the target amount of electrical charge.

The controller may be configured to predict the available current of the next time slot to be greater than a predicted available current of the current time slot, in response to an increase in a degree to which the amount of output current of the converter in the current time slot is greater than the amount of output current of the converter in the previous time slot.

Weights respectively applied to the difference between the amount of electrical charge stored in the capacitor in the current time slot and the target amount of electrical charge, and to the change in the amount of output current of the converter, may be determined based on a stability condition of a delayed differential equation for the available current of the next time slot.

The controller may be configured to predict the available current of the next time slot based on an available current of a current time slot.

The controller may be configured to determine operation modes of blocks in the load system based on any one or any combination of any two or more of a deadline, a hardware resource, and a task priority of an execution task for each of the blocks in the load system such that a consumed current of the load system matches the available current.

The controller may be configured to determine operation modes of blocks in the load system based on a consumed current table corresponding to operation modes of the blocks such that a consumed current of the load system matches the available current.

The consumed current table corresponding to the operation modes of the blocks in the load system may include any one or any combination of any two or more of: a consumed current table corresponding to an operating frequency of a microcontroller unit (MCU) included in the load system; a consumed current table corresponding to a transmission power and a communication frequency of a communication block included in the load system; and a consumed current table corresponding to an operation mode and an operating frequency of a periphery block included in the load system.

The periphery block may include either one or both of a sensor and a hardware accelerator.

The device may be an implantable medical device.

The controller may be configured to preferentially allocate a portion of the determined consumed current to blocks in the load system except for a microcontroller unit (MCU) among the blocks in the load system and control an operating frequency of the MCU based on a remaining portion of the determined consumed current.

An interval of the next time slot and a delay occurring when the determined consumed current of the load system is applied to the load system may be determined based on a voltage ripple and a capacitance of the capacitor.

The device may further include: a maximum power point (MPP) tracker (MPPT) configured to track an MPP at which a maximum electric energy is generated in the photovoltaic module to adjust an input impedance of the converter.

A maximum value of an electric energy generated in the photovoltaic module may be obtained from an open circuit voltage of the photovoltaic module using a function between the maximum value of the electric energy and an open circuit voltage determined through an exponential curve fitting.

In another general aspect, a processor-implemented power control method of a microelectronic device includes: predicting an available current of a next time slot based on an output current of a converter connected to a photovoltaic module and an amount of electrical charge of a capacitor configured to store an electric energy transferred from the converter; and determining a consumed current of a load system of the next time slot based on the predicted available current.

The predicting of the available current may include predicting the available current of the next time slot based on any one or any combination of any two or more of: a change in an amount of electrical charge stored in the capacitor from a previous time slot to a current time slot; a difference between the amount of electrical charge stored in the capacitor in the current time slot and a target amount of electrical charge to be stored in the capacitor; and a change in an amount of output current of the converter from the previous time slot to the current time slot.

The method may include: measuring an open circuit voltage of the photovoltaic module that converts a light energy into an electric energy; determining a maximum value of an electric energy generated in the photovoltaic module from the open circuit voltage; and determining the output current of the converter based on the maximum value of the electric energy.

The method may include: determining, based on a voltage of the capacitor, the amount of electrical charge stored in the capacitor.

The photovoltaic module may be configured to convert a light energy into an electric energy, the converter may be configured to convert a voltage output from the photovoltaic module into a predetermined voltage, and a controller may be configured to perform the predicting of the available current and the determining of the consumed current.

Other features and aspects will be apparent from the following detailed description, the drawings, and the claims.

Figure 1:
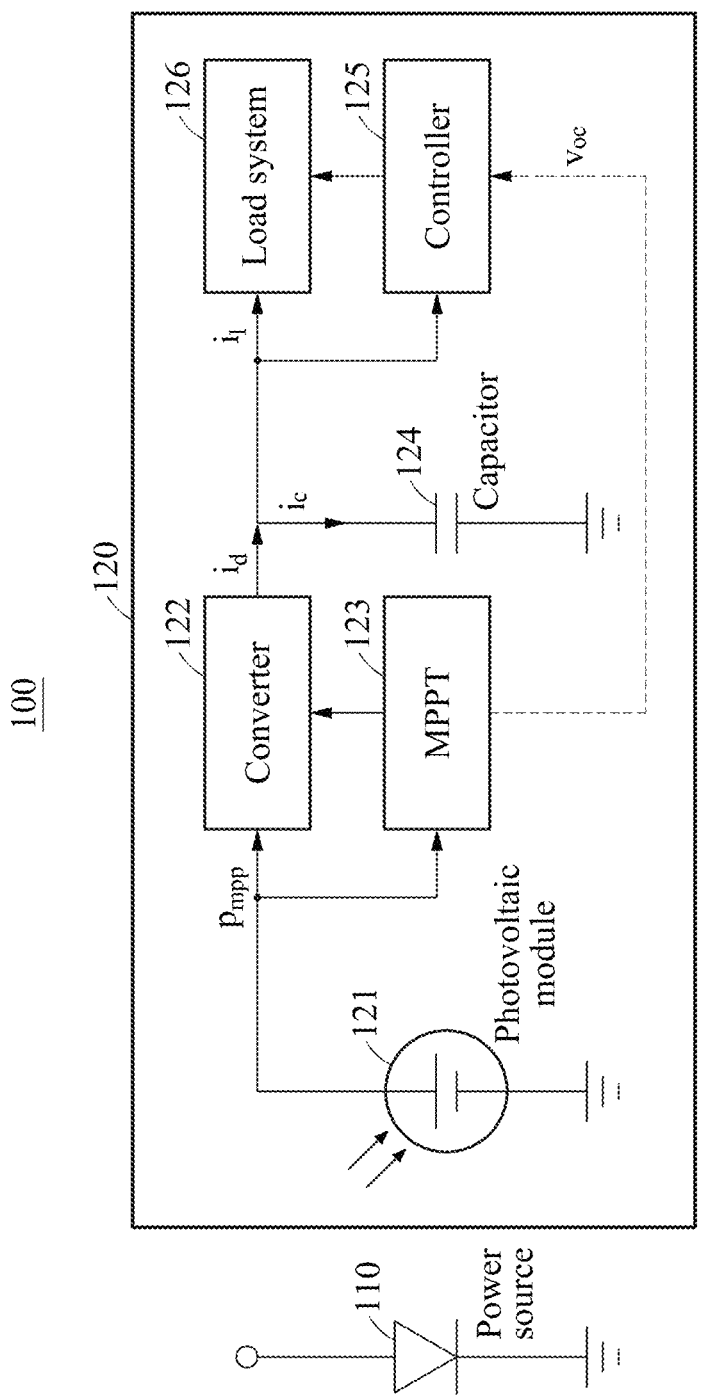
FIG. 1 illustrates an example of a photovoltaic system.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Unless otherwise defined, all terms, including technical and scientific terms, used herein have the same meaning as commonly understood by one of ordinary skill in the art to which this disclosure pertains and after an understanding of the disclosure of this application. Terms, such as those defined in commonly used dictionaries, are to be interpreted as having a meaning that is consistent with their meaning in the context of the relevant art and the disclosure of this application, and are not to be interpreted in an idealized or overly formal sense unless expressly so defined herein.

FIG. 1 is a diagram illustrating an example of a photovoltaic system.

Referring to FIG. 1, a photovoltaic system 100 includes a power source 110 and a small device 120. The small device 120 may include a photovoltaic module 121, a converter 122, a maximum power point tracker (MPPT) 123, a capacitor 124, a controller 125, and a load system 126.

The power source 110 is a source for supplying an energy to the small device 120. The power source 110 may include a natural light source and/or an artificial light source such as light-emitting diode (LED) and laser. The power source 110 may transfer a light energy to the small device 120.

The small device 120 may be a device configured to operate based on the light energy received from the power source 110. For example, the small device 120 may operate using an energy wirelessly received from an outside such that the device 120 may operate without a battery to thereby minimize a size of the device 120. Thus, the small device 120 may be a microelectronic apparatus, which may further include, or may be, an implantable medical device inserted into a human body for medical purposes, an electroceutical, a crypto anchor for preventing cloning, and/or a smart dust to be used as an ultra-small sensor (e.g., a microelectromechanical sensor).

The photovoltaic module 121 converts the light energy received from the power source 110 into an electric energy. The electric energy generated in the photovoltaic module 121 may vary based on, for example, a temperature of the photovoltaic module 121, an irradiation condition received by the photovoltaic module 121, and/or an input impedance of the converter 122. As such, since an output voltage of the photovoltaic module 121 may vary based on various factors, voltage stabilization may be conducted by using the converter 122 instead of directly connecting the load system 126 to the photovoltaic module 121, to account for the variance of the output voltage of the photovoltaic module 121. The photovoltaic module 121 may operate as a current source. However, when an input impedance increases, a voltage may gradually decrease such that the photovoltaic module 121 operates as a voltage source. In this disclosure, the term "electric energy" may also be referred to as the term "power".

The converter 122 may be a direct current (DC)-to-DC converter that converts a voltage output from the photovoltaic module 121 into a predetermined voltage. For example, the converter 122 may convert a variable voltage output from the photovoltaic module 121 into a fixed voltage. The converter 122 may regulate an unstable or varying output voltage of the photovoltaic module 121 and adjust an input impedance to increase or maximize a harvesting efficiency of the photovoltaic module 121. Also, herein, it is noted that use of the term "may" with respect to an example or embodiment, e.g., as to what an example or embodiment may include or implement or how an example or embodiment may be configured, means that at least one example or embodiment exists where such a feature is included, implemented, and/or configured while all examples and embodiments are not limited thereto.

A point at which a maximum electric energy is generated in the photovoltaic module 121 may be referred to as a maximum power point (MPP). The maximum power point tracker (MPPT) 123 tracks the MPP. The MPP may vary based on an irradiation condition (such as a light intensity and/or an optical channel condition) received in the photovoltaic module 121 and a temperature of the photovoltaic module 121. The MPPT 123 may periodically track the varying MPP to adjust an input impedance of the converter 122 connected to the photovoltaic module 121 such that the maximum electric energy is generated in the photovoltaic module 121.

The capacitor 124 stores the electric energy transferred from the converter 122. For example, when the small device 120 has a millimeter-scale, the capacitor 124 may have several tens of microfarads (μF). The capacitor 124 may buffer a harvested energy to provide stable power to the load system 126.

The controller 125 adjusts power consumption of the load system 126, for example, in real time based on an amount of harvested energy in the photovoltaic module 121, thereby ensuring consecutive operations and achieving a maximum performance. The controller 125 may predict an available current of a next time slot based on the electric energy stored in the capacitor 124 and determine a consumed current (for example, a load current of the load system 126) based on the predicted available current. A process of predicting, by the controller 125, the available current of the next time slot and determining the consumed current of the load system 126 will be further described below.

The load system 126 may include blocks for performing various application services based on the harvested energy. The load system 126 may include a microcontroller unit (MCU), a communication block, and a periphery block, as non-limiting examples. The periphery block may include, for example, a sensor and a hardware accelerator. The MCU may be a processor for controlling the blocks in the load system 126.

Operating frequencies of the blocks included in the load system 126 and whether the blocks operate may be determined by the controller 125, so that the controller 125 controls an energy consumed in the load system 126.

The small device 120 may have a size-independent energy reception efficiency through the photovoltaic module 121. Also, by using a lens, light may be concentrated on a small area of the photovoltaic module 121, so that an ultra-small device may receive a large amount of energy. The small device 120 may effectively overcome an issue of a low wireless power efficiency due to restrictions on a size of an antenna in a typical wireless power transmission-based small device using a radio frequency (RF) band and an issue of typical RF-based wireless power transmission acting as large noise in a sensor.

In FIG. 1, $p_{mpp}$ denotes a maximum electric energy of the photovoltaic module 121, $i_d$ denotes an output current of the converter 122, $i_c$ denotes a current of the capacitor 124, $i_l$ denotes an available current of the load system 126, and $v_{oc}$ denotes an open circuit voltage of the photovoltaic module 121.

Also, in response to the controller 125 controlling all harvested energy to be consumed in the load system 126, a voltage of the capacitor 124 may be maintained at a predetermined level. Accordingly, the available current of the next time slot is proportional to an available energy. Matching the consumed current of the load system 126 to the available current may also be expressed as matching the consumed energy of the load system 126 to the available energy.

Figure 2:
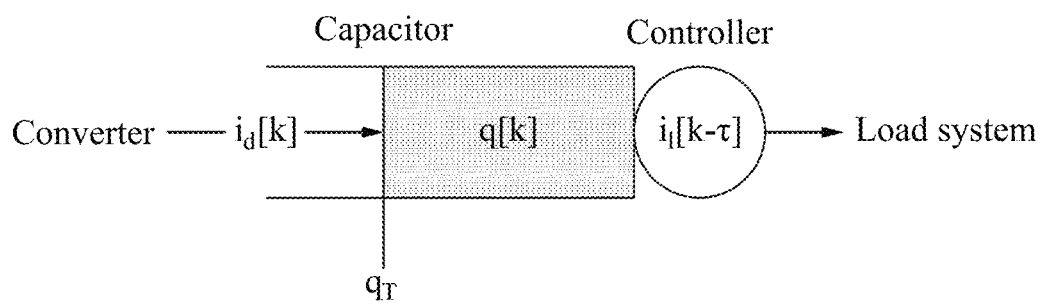
FIG. 2 illustrates an example of a queuing model of an amount of electrical charge stored in a capacitor.

FIG. 2 illustrates an example of a queuing model of an amount of electrical charge stored in a capacitor.

Referring to FIG. 2, a queuing model 200 is represented by an amount of electrical charge q[k] stored in a capacitor, a current $i_d[k]$ input from a converter, and a current $i_\ell[k-T]$ output to a load system.

The capacitor functions as a queue that stores an electrical charge output from the converter and provides the stored electrical charge when the load system requires the electrical charge. The queuing model 200 may be a discrete time-based model, for example. In FIG. 2, k denotes a $k^{th}$ time slot, each time slot has an interval of T seconds, and the queuing model 200 is updated at intervals of T seconds. $q_T$ is a target amount of electrical charge to be stored by a controller in the capacitor. When the amount of electrical charge q[k] stored in the capacitor is constantly maintained by the controller, an output current of the converter may be the same as a consumed current of the load system in a steady state. In other words, the controller may consistently track a harvested energy and control all of the harvested energy to be consumed in the load system, thereby constantly maintaining the amount of electrical charge stored in the capacitor and maintaining a voltage of the capacity at a predetermined level.

The queuing model 200 may be expressed by Equation 1 as shown below, for example.

$$q[k+1]=q[k]+T(i_d[k]-i_\ell[k-\mathcal{T}])  \quad \text{Equation 1:}$$

In Equation 1, $\mathcal{T}$ denotes a value of a delay required to actually reflect a consumed current of the load system controlled by the controller. Unlike an analog system, a delay may occur in a digital system in a process of adjusting the consumed current of the load system after an available current to be used in a next time slot is predicted in the controller. As non-limiting examples, delay may include any one or any combination of any two or more of a time required for a clock source to generate a stable output to apply dynamic frequency scaling, a time required to store and recover a processor status for dynamic power management, a time for which a digital logic delays a load control on a non-preemptive task such as an input and output (IO) operation, an additional time required for the load system to complete a current task, and a time required to apply a change in consumed current of the load system.

Figure 3:
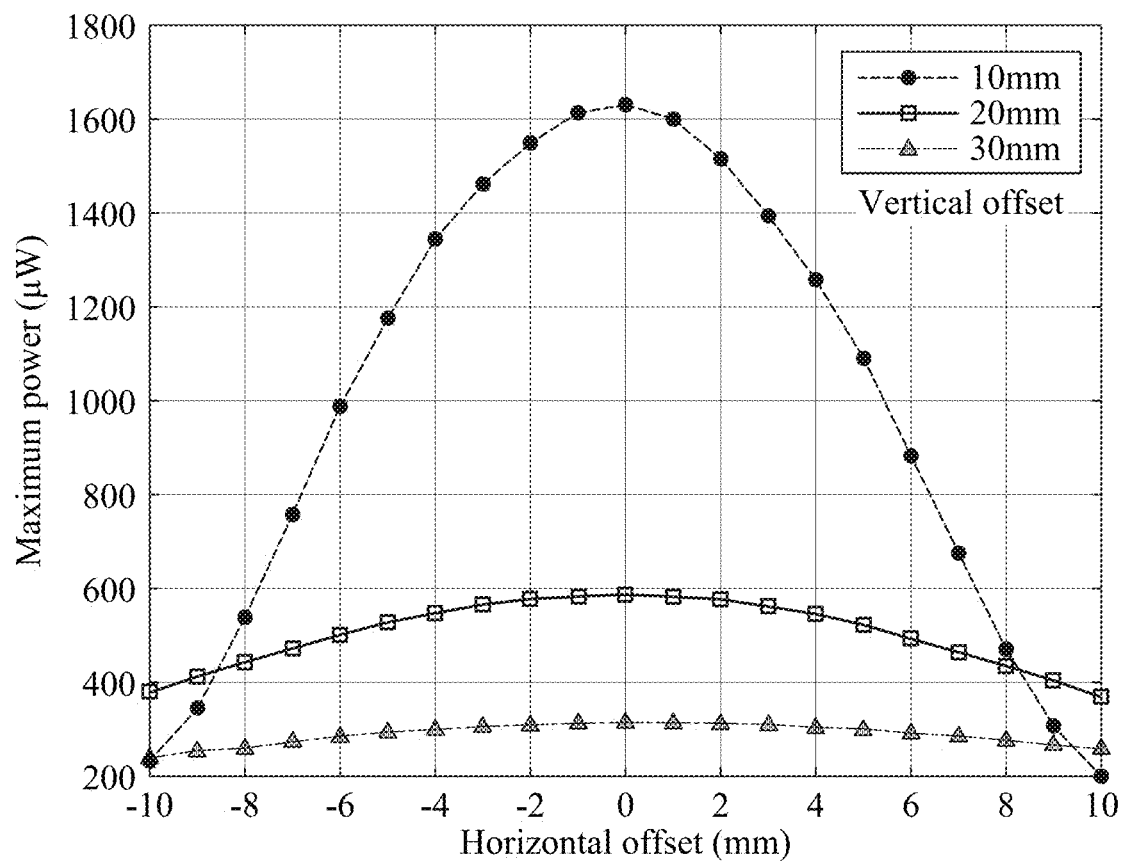
FIGS. 3 and 4 illustrate examples of a maximum value of an electric energy generated in a photovoltaic module.
Figure 4:
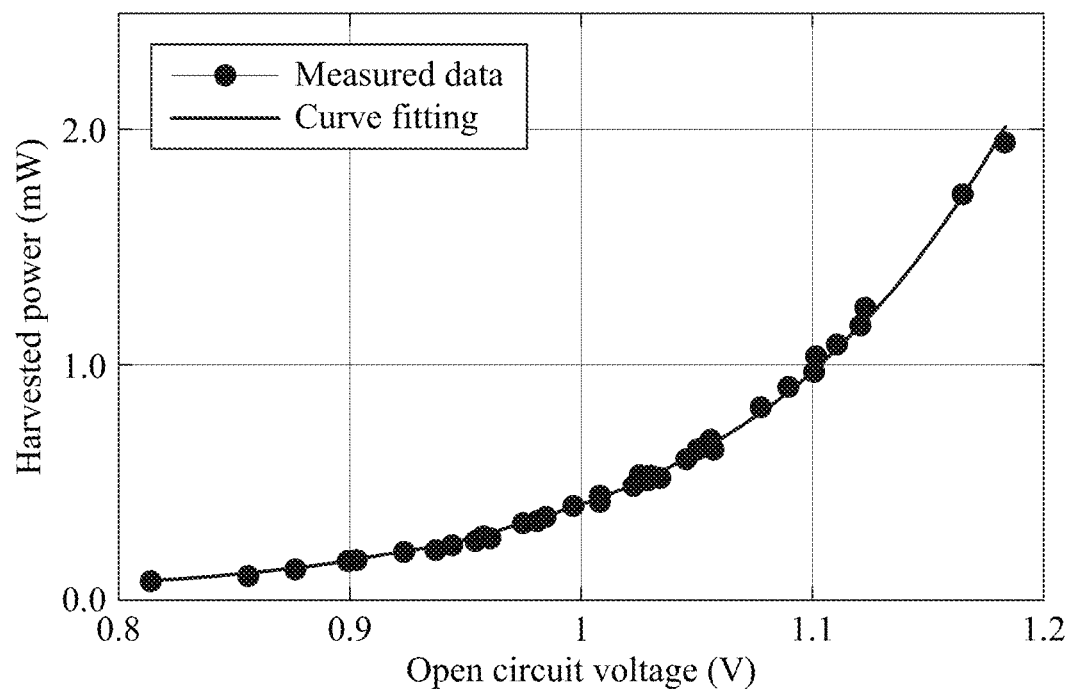

FIGS. 3 and 4 illustrate examples of a maximum value of an electric energy generated in a photovoltaic module.

As described with reference to FIG. 1, an MPPT consistently changes an input impedance of a converter to maximize an electric energy generated in a photovoltaic module. A maximum electric energy generated by the photovoltaic module in a $k^{th}$ time slot is denoted by $P_{mpp}[k]$. When an energy conversion efficiency of the converter is η[k] and an output voltage of the converter is $v_d$ in the $k^{th}$ time slot, an output current $i_d[k]$ of the converter is expressed as follows.

$$i_d[k] = \frac{\eta[k] \cdot p_{mpp}[k]}{v_d}  \quad \text{Equation 2}$$

In Equation 2, the energy conversion efficiency η[k] of the converter may change based on a time slot, which may be due to an energy consumed in the converter or the MPPT. For example, as the output energy of the converter increases, the energy conversion efficiency η[k] of the converter increases. Conversely, as the output energy of the converter decreases, the energy conversion efficiency η[k] of the converter decreases. Hereinafter, a maximum electric energy generated by such a photovoltaic module will be described in detail with reference to FIGS. 3 and 4.

FIG. 3 illustrates an example of a maximum value of an electric energy generated in a photovoltaic module based on horizontal and vertical offsets.

Graphs of FIG. 3 represent a horizontal offset which is a distance that a white LED deviates or misaligns from a center of the photovoltaic module (e.g., a center point or center normal of a light-absorbing surface of the photovoltaic module) when the white LED is illuminated on the photovoltaic module, and a change in maximum power generated in the photovoltaic module based on the distance between the white LED and the center of the photovoltaic module. As shown in the graph of FIG. 3, at least 200 microwatts (μW) and up to 1600 μW or more of power may be generated at a maximum center error of 10 millimeters (mm) and a maximum distance 30 mm. When a small device (e.g., the small device 120) is driven using an LED light of a smartphone, the maximum power generated in the photovoltaic module may change significantly even with a small movement. Thus, in the small device without a battery or supercapacitor, it may be important to accurately predict a harvested energy varying on a time-by-time basis so as to be consumed in the load system, which may increase a system stability. For this, a maximum value of the electric energy generated in the photovoltaic module may be predicted.

FIG. 4 illustrates an example of a function between an open circuit voltage and a maximum value of an electric energy.

For certain devices, a characteristic of a photovoltaic module may be represented by a I-V characteristic curve. However, in terms of a small device, it may be difficult to accurately predict irradiation power of a light source reaching the photovoltaic module. Also, when an artificial light source such as an LED is used, the light source may not uniformly reach the photovoltaic module. Thus, it may be difficult to obtain an accurate I-V characteristic curve for the small device. Accordingly, an open circuit voltage of the photovoltaic module may instead be measured for the small device, so that a maximum value of an electric energy generated in the photovoltaic module may be predicted by deriving a relationship between the open circuit voltage and the maximum value of the electric energy. According to measured data shown in FIG. 4, a harvested energy drastically increases as the open circuit voltage increases. A graph of FIG. 4 shows a result of curve fitting performed on experimental data of the open circuit voltage and the maximum value of the electric energy using an exponential function, and may be expressed by Equation 3 below, for example.

$$p_{mpp}[k]=\alpha \cdot \exp(\beta \cdot v_{oc}[k])  \quad \text{Equation 3:}$$

Varying examples exist with varying photovoltaic modules having different characteristics, for example, in Equation 3, α and β have been derived through experiment for an example photovoltaic module. For example, through the experiment, α may be determined to be 0.063 and β may be determined to be 8.763.

The maximum value of the electric energy generated in the photovoltaic module may be predicted by using the function between the open circuit voltage and the maximum value of the electric energy determined through the exponential curve fitting. Also, by substituting the maximum value of the electric energy into Equation 2, a current $i_d[k]$ input to the capacitor in the $k^{th}$ time slot may be obtained.

As such, since the maximum electric energy generated in the photovoltaic module considerably varies based on the optical channel condition, the open circuit voltage may be measured for each time slot to predict the maximum value of the electric energy of the photovoltaic module.

Figure 5:
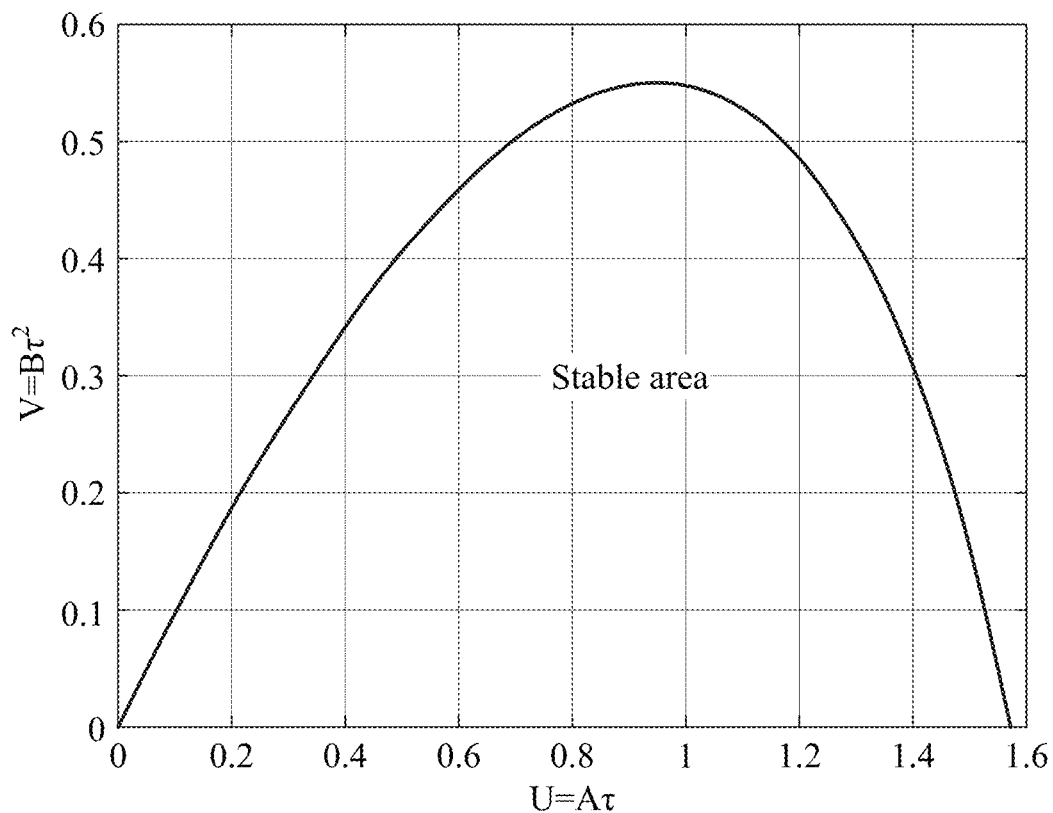
FIGS. 5 and 6 illustrate examples of a stability condition of a delayed differential equation for an available current of a next time slot.
Figure 6:
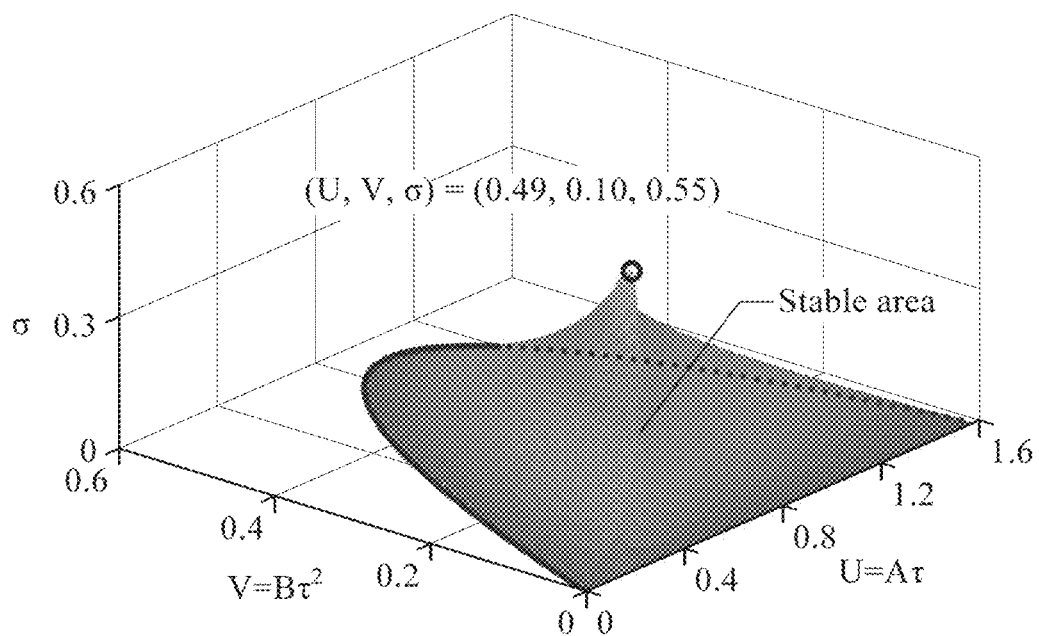

FIGS. 5 and 6 illustrate examples of a stability condition of a delayed differential equation for an available current of a next time slot.

A controller may predict an available current of a next time slot using Equation 4 as shown below, for example.

$$i_\ell[k+1]=i_\ell[k]+A(q[k]-q[k-1])+BT(q[k]-q_T)+(i_d[k]-i_{d[k-1]})  \quad \text{Equation 4:}$$

An available current $i_\ell[k+1]$ of a next time slot may be determined based on a change q[k]−q[k−1] in an amount of electrical charge stored in a capacitor, a difference $q[k]-q_T$ between an amount of electrical charge stored in the capacitor and a target amount of electrical charge to be stored in the capacitor, and a change $i_d[k]-i_d[k-1]$ in an amount of output current of a converter.

According to Equation 4, as a degree to which an amount of electrical charge of a current time slot stored in the capacitor is greater than an amount of electrical charge of a previous time slot increases, a predicted available current of the next time slot increases. For example, when a greater amount of electrical change is generated in the current time slot in comparison to the previous time slot, a relatively great amount of available current may be determined such that more electrical charge is transferred to a load system.

In addition, as a degree to which the amount of electrical charge stored in the capacitor is greater than the target amount of electrical charge increases, a predicted available current of the next time slot increases. For example, when the amount of electrical charge stored in the capacitor is greater than the target amount of electrical charge, a great amount of electrical charge may be determined for the next time slot so that more electrical charge corresponding to excess electrical charge is transferred to the load system. Conversely, for example, when the amount of electrical charge stored in the capacitor is less than the target amount of electrical charge, a small amount of electrical charge may be determined for the next time slot so that more electrical charge is stored in the capacitor.

Also, as a degree to which an amount of output current output from the converter in the current time slot is greater than an amount of output current of the previous time slot increases, a predicted available current of the next time slot increases. For example, when the amount of output current output from the converter in the current time slot is greater than the amount of output current of the previous time slot, a greater amount of electrical change may flow into the capacitor in the current time slot in comparison to the previous time slot. In this example, a great amount of electrical charge may be determined for the next time slot so that more electrical charge corresponding to excess electrical charge is transferred to the load system.

Here, A and B may each be a constant, and a weight indicating an influence of a corresponding term in predicting $i_l[k+1]$. To accurately predict the available current of the next time slot, the controller may obtain the weights A and B as shown below.

When it is assumed that a queuing dynamic update interval T is infinitely small, Equations 1 and 4 may be expressed as continuous functions as follows, for example.

$$q'(t)=i_d(t)-i_\ell(t-\mathcal{T}) \quad i'_\ell(t)=Aq'(t)-B\{q(t)-q_T\}+i'_d(t) \quad \text{Equation 5:}$$

The above equations may be summarized by Equation 6 as shown below, for example.

$$q''(t) + Aq'(t-\tau) + B\{q(t-\tau) - q_T\} + i'_d(t-\tau) - i'_d(t) = 0 \quad \text{Equation 6}$$

In Equation 6, a delay $\mathcal{T}$ may not exceed several tens of milliseconds, a derived function of $p_{mpp}[k]$ may not significantly change within several milliseconds, and $p_{mpp}[k]$ may be proportional to $i_d[k]$ in Equation 2. Thus, $i'_d(t-\mathcal{T})$ and $i'_d(t)$ may have similar values. Accordingly, last two terms may be neglected in Equation 6.

When an error function is defined by $\delta(t)=q(t)-q_T$ and a new variable $t=\mathcal{T}\xi$, Equation 6 may be summarized by a delayed differential equation as shown by Equation 7 below, for example.

$$\delta''(\xi)+A\delta'(\xi-1)+B\delta(\xi-1)=0 \quad \text{Equation 7:}$$

In order for q(t) to converge to a predetermined value over time, a value of a real number of a root in a characteristic function solution of the delayed differential equation may be a negative value. According to a stability condition of the delayed differential equation, an area of the constants in which the delayed differential equation stably functions may be as shown by Equation 8 below, for example.

$$0 < U < \frac{\pi}{2} \quad \text{Equation 8}$$

and $$0 < V < \omega_1^2 \sqrt{1 - \left(\frac{U}{\omega_1}\right)^2}$$

$$U = A_\tau$$

$$V = B_\tau^2$$

In Equation 8, $w_1$ is a unique solution of $U=w \sin w$ in an interval $$\left(0, \frac{\pi}{2}\right).$$

FIG. 5 illustrates an area in which the delayed differential equation is stable for values of the constants A and B.

Since all real number values in the stable area of the characteristic function solution of the delayed differential equation are negative, a convergence rate of q(t) may be the fastest when a real number part of a principal root of a characteristic function is the smallest, for example, when a negative absolute value is the greatest. Since a closed-form solution of the characteristic function is absent, the real number part of the principal root may be calculated for the values of A and B in the stable area using a numerical method a illustrated in FIG. 6. For example, the convergence rate may be the fastest when the value of $(U=A_T, V=B_T^2)$ is (0.49, 0.10). In FIG. 6, σ denotes an asymptotic decay rate.

Figure 7:
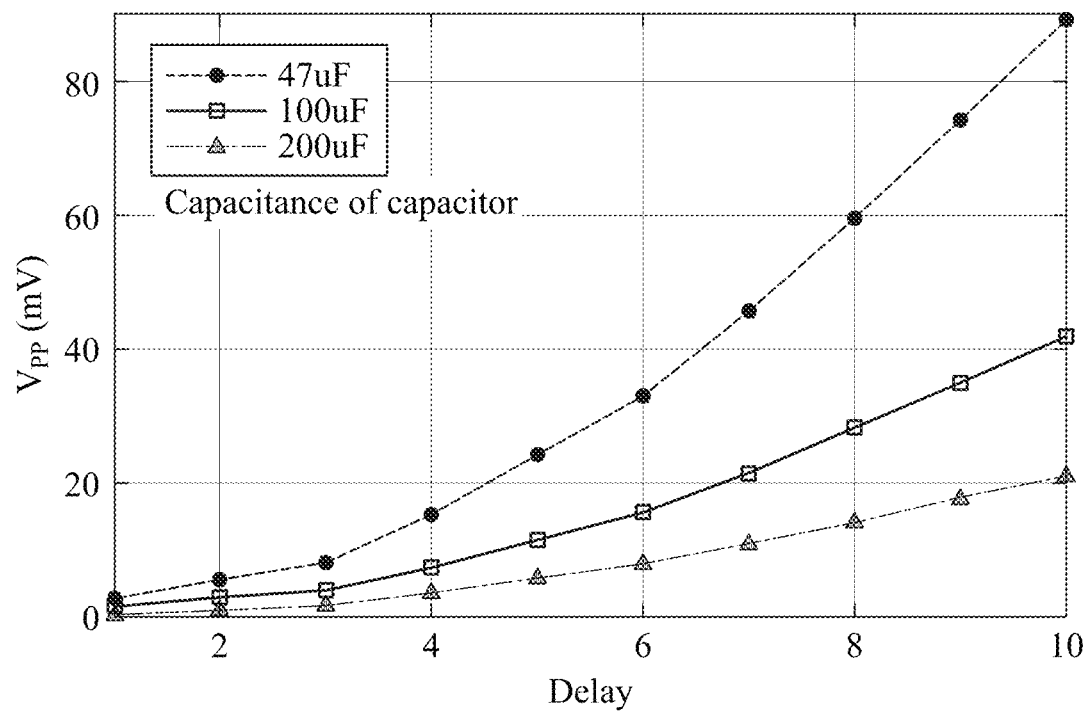
FIGS. 7 and 8 illustrate examples of a voltage ripple of a capacitor.
Figure 8:
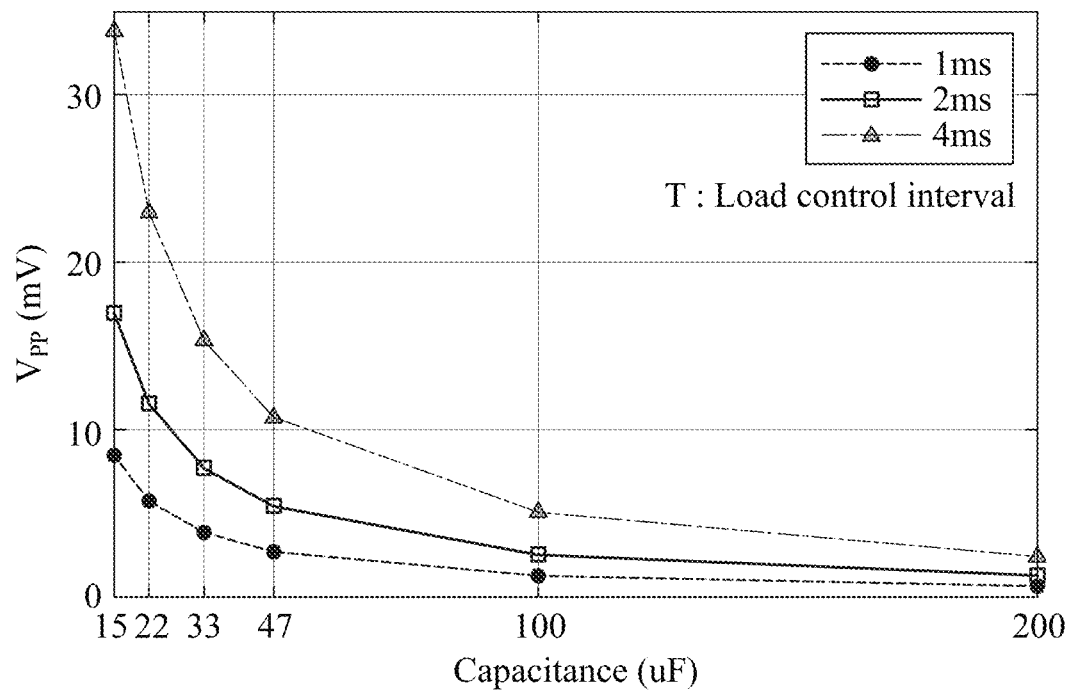

FIGS. 7 and 8 illustrate examples of a voltage ripple of a capacitor.

FIGS. 7 and 8 illustrate a change in voltage ripple of a capacitor based on a delay $\mathcal{T}$, an interval T of a time slot, and a capacitance of the capacitor. The delay $\mathcal{T}$ is proportional to the interval T. As the delay $\mathcal{T}$ increases, the interval T of the time slot increases, and as the capacitance of the capacitor decreases, the voltage ripple increases. Conversely, as the delay $\mathcal{T}$ decreases, the interval T of the time slot decreases, and as the capacitance of the capacitor increases, the voltage ripple decreases. Accordingly, in a small device without a battery (e.g., the small device 120), when conditions of the capacitance of the capacitor and the voltage ripple are given, the delay $\mathcal{T}$ and the interval T of the time slot satisfying the corresponding voltage ripple may be determined.

Figure 9:
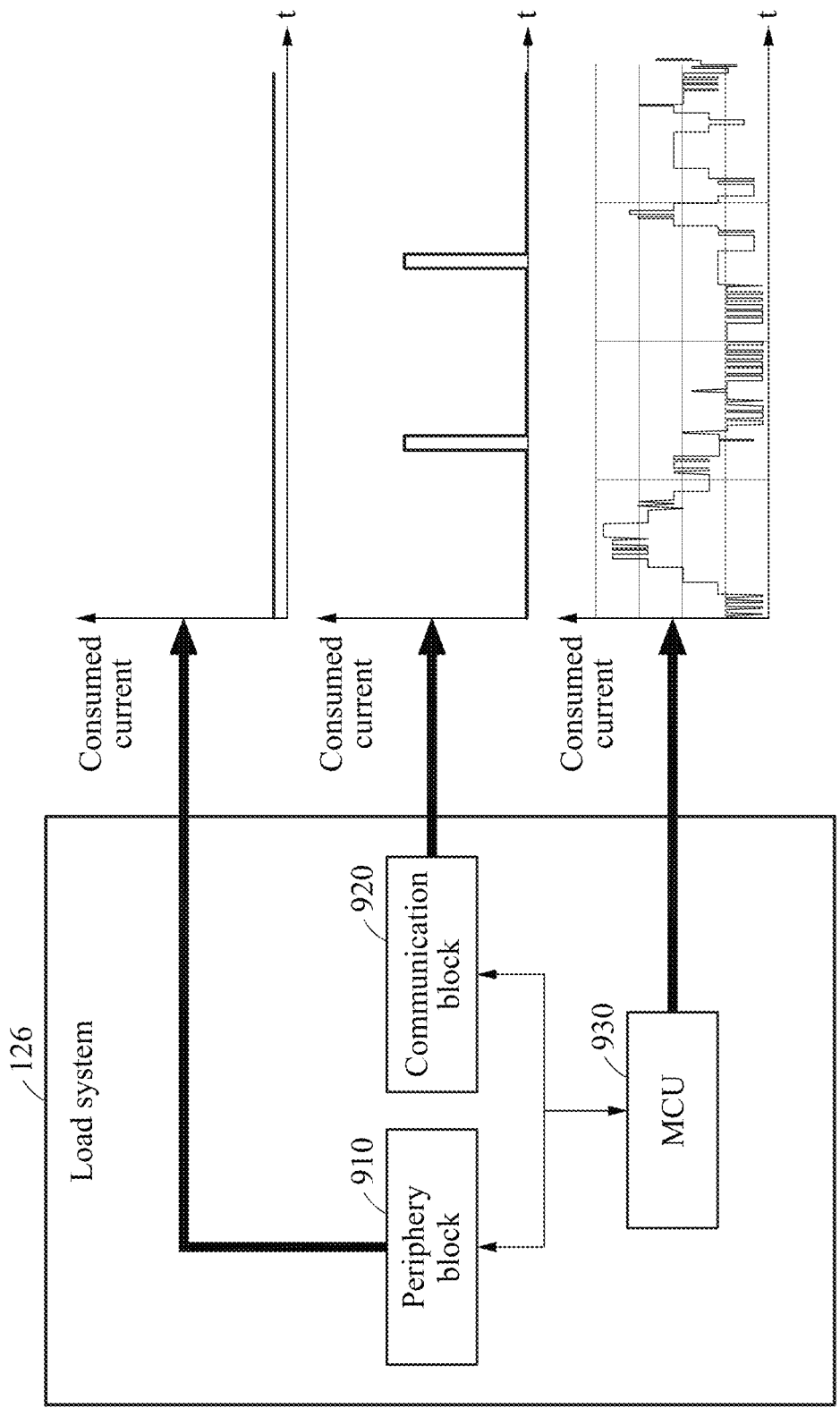
FIG. 9 illustrates an example of determining a current consumed in a load system.

FIG. 9 illustrates an example of determining a current consumed in a load system.

Referring to FIG. 9, the load system 126 may include a periphery block 910, a communication block 920, and an MCU 930. A current to be consumed in each of the blocks in the load system 126 may be determined by a controller (e.g., the controller 125).

The controller may determine operation modes of each block in the load system 126 based on at least one of a deadline, a hardware resource, and a task priority of an execution task for each block in the load system 126 such that a consumed current of the load system 126 matches the available current. the load system 126. Here, the operation modes include an active mode and a sleep mode.

In one example, when the deadline of the execution task is imminent, the controller may allocate the consumed current to a block performing the execution task with priority and allocate a remaining consumed current to a block performing an execution task with a deadline that is not imminent. In addition, the controller may allocate the consumed current to a block having small hardware resources with priority and allocate a remaining consumed current to a block having large hardware resources. Also, the controller may allocate the consumed current to a block with a high level of task priority and allocate a remaining consumed current to a block with a lower level of task priority.

In another example, the controller may determine operation modes of blocks in the load system 126 based on a consumed current table corresponding to operation modes of the blocks such that a consumed current of the load system 126 matches the available current. The consumed current table corresponding to the operation modes of the blocks in the load system 126 may include any one or any combination of any two or more of a consumed current table corresponding to an operating frequency of the MCU 930 included in the load system 126, a consumed current table corresponding to a transmission power and a communication frequency of the communication block 920 included in the load system 126, and a consumed current table corresponding to an operation mode and an operating frequency of the periphery block 910 included in the load system 126.

In another example, the controller may preferentially allocate a consumed current to the periphery block 910 instead of the MCU 930 among the blocks in the load system 126 and control an operating frequency of the MCU 930 based on a remaining consumed current. For example, since it may be important for a sensor included in the periphery block 910 to sense at a predetermined time and so the sensor may not use a large amount of consumed energy for sensing, the consumed current may be allocated to the periphery block 910 with priority. Also, the communication block 920 may be controlled to only periodically transmit sensed data to an outside, and thus may not require a consumed current that would otherwise be needed for real-time/constant communication. Therefore, the consumed current may be allocated to the communication block subsequently. Also, since the consumed current of the MCU 930 may vary based on the operating frequency, the MCU 930 may perform processing at a high operating frequency when a large amount of consumed current remains and perform processing at a low operating frequency when a small amount of consumed current remains. Since a remaining consumed current may be allocated to the MCU 930 after the consumed current is allocated to the periphery block 910 and the communication block 920, the consumed current allocated to the MCU 930 may have a similar graph to that of an amount of energy harvested from the photovoltaic module.

Figure 10:
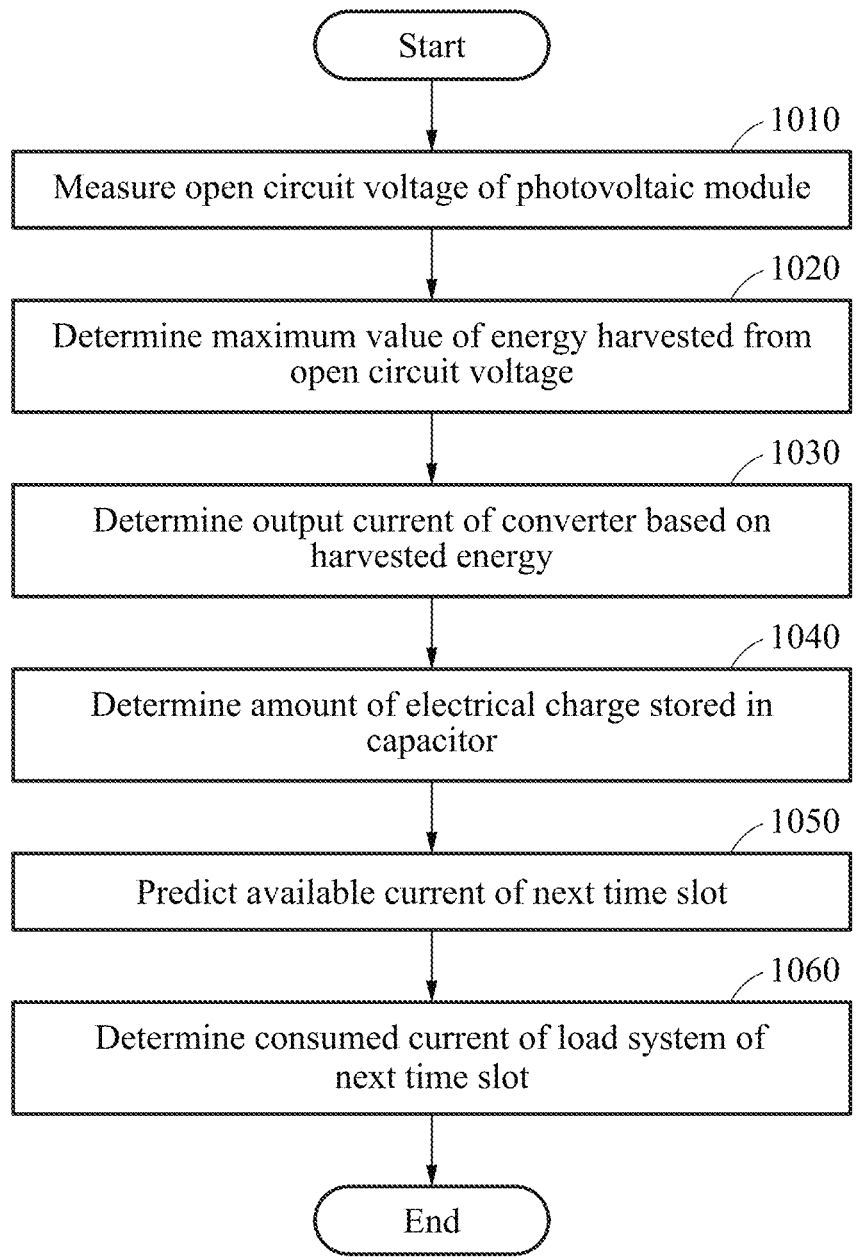
FIG. 10 illustrates an example of a power control method.

FIG. 10 illustrates an example of a power control method.

Referring to FIG. 10, the power control method may be performed by a controller (e.g., the controller 125) included in a small device (e.g., the small device 120).

In operation 1010, the small device may measure an open circuit voltage $v_{oc}[k]$ of a photovoltaic module (e.g., the photovoltaic module 121). The photovoltaic module may be disconnected for a short period of time in which an open circuit voltage of the photovoltaic module is measured.

In operation 1020, the small device may determine a harvested energy $p_{mpp}[k]$ from the open circuit voltage $v_{oc}[k]$. In an example, Equation 3 may be used to determine the harvested energy $p_{mpp}[k]$.

In operation 1030, the small device may determine an output current $i_d[k]$ of a converter (e.g., the converter 122) from the harvested energy $p_{mpp}[k]$. In an example, Equation 1 may be used to determine the output current $i_d[k]$.

In operation 1040, the small device may measure a voltage $v_c[k]$ of a capacitor (e.g., the capacitor 124) and determine an amount of electrical charge $q[k]$ stored in the capacitor. In an example, $q[k]=C \cdot v_c[k]$ may be used to determine the amount of electrical charge $q[k]$.

In operation 1050, the small device may predict an available current $i_l[k+1]$ of a next time slot based on the output current $i_d[k]$ of the converter connected to the photovoltaic module and the amount of electrical charge $q[k]$ of the capacitor storing the electric energy transferred from the converter. In an example, Equation 4 may be used to predict the available current $i_l[k+1]$.

In operation 1060, the small device may determine a consumed current (for example, a load current of a load system) of the next time slot based on the available current. For example, when the load system includes a processor, an operating frequency $f[k+1]$ of the processor in the next time slot may be as follows.

$$f[k+1]=\lfloor i_l[k+1]/\rho \rfloor \qquad \text{Equation 9:}$$

In Equation 9, $\lfloor x \rfloor$ is a bottom function representing a maximum integer smaller than x.

Operations 1010 through 1060 may be performed repetitively in each time slot.

The power sources, small devices, photovoltaic modules, converters, MPPTs, capacitors, controllers, load systems, periphery blocks, communication blocks, MCUs, control units, blocks, modules, power source 110, small device 120, photovoltaic module 121, converter 122, MPPT 123, capacitor 124, controller 125, load system 126, periphery block 910, communication block 920, MCU 930, and other apparatuses, units, modules, devices, and other components described herein with respect to FIGS. 1-10 are implemented by or representative of hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-10 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions used herein, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A microelectronic device, comprising:
 a converter configured to convert a voltage of an electric energy into a predetermined voltage;
 a capacitor configured to store an electric energy transferred from the converter; and
 a controller configured to
  measure an amount of electrical charge of the capacitor in a current time slot, predict an available current of a next time slot based on an output current of the converter and the measured amount of electrical charge of the capacitor in the current time slot, and determine a consumed current of a load system of the next time slot to match the predicted available current, wherein an impedance of the converter is adjusted to maximize the electric energy and a delay occurring when the determined consumed current of the load system is applied to the load system is determined based on a voltage ripple and a capacitance of the capacitor.

2. The device of claim 1, wherein the controller is configured to predict the available current of the next time slot based on any one or any combination of any two or more of:

a determined change in an amount of electrical charge stored in the capacitor from a previous time slot to the current time slot;

a determined difference between the amount of electrical charge stored in the capacitor in the current time slot and a target amount of electrical charge to be stored in the capacitor; and a determined change in an amount of output current of the converter from the previous time slot to the current time slot.

3. The device of claim 2, wherein the controller is configured to predict the available current of the next time slot to be greater than a predicted available current of the current time slot, in response to an increase in a degree to which the amount of electrical charge stored in the capacitor in the current time slot is greater than the amount of electrical charge stored in the capacitor in the previous time slot.

4. The device of claim 2, wherein the controller is configured to predict the available current of the next time slot to be greater than a predicted available current of the current time slot, in response to an increase in a degree to which the amount of electrical charge stored in the capacitor in the current time slot is greater than the target amount of electrical charge.

5. The device of claim 2, wherein the controller is configured to predict the available current of the next time slot to be greater than a predicted available current of the current time slot, in response to an increase in a degree to which the amount of output current of the converter in the current time slot is greater than the amount of output current of the converter in the previous time slot.

6. The device of claim 2, wherein weights respectively applied to the difference between the amount of electrical charge stored in the capacitor in the current time slot and the target amount of electrical charge, and to the change in the amount of output current of the converter, are determined based on a stability condition of a delayed differential equation for the available current of the next time slot.

7. The device of claim 1, wherein the controller is configured to predict the available current of the next time slot based on an available current of the current time slot.

8. The device of claim 1, wherein the controller is configured to determine operation modes of blocks in the load system based on any one or any combination of any two or more of a deadline, a hardware resource, and a task priority of an execution task for each of the blocks in the load system such that a consumed current of the load system matches the available current.

9. The device of claim 1, wherein the controller is configured to determine operation modes of blocks in the load system based on a consumed current table corresponding to operation modes of the blocks such that a consumed current of the load system matches the available current, wherein the consumed current table include information of a current amount to be consumed in a respective mode of each block, of the blocks, in the load system.

10. The device of claim 9, wherein the consumed current table corresponding to the operation modes of the blocks in the load system comprises any one or any combination of any two or more of:

a consumed current table corresponding to an operating frequency of a microcontroller unit (MCU) included in the load system;

a consumed current table corresponding to a transmission power and a communication frequency of a communication block included in the load system; and a consumed current table corresponding to an operation mode and an operating frequency of a periphery block included in the load system.

11. The device of claim 10, wherein the periphery block includes either one or both of a sensor and a hardware accelerator.

12. The device of claim 1, wherein the controller is configured to preferentially allocate a portion of the determined consumed current to blocks in the load system except for a microcontroller unit (MCU) among the blocks in the load system and control an operating frequency of the MCU based on a remaining portion of the determined consumed current.

13. The device of claim 1, wherein the device is an implantable medical device.

14. A microelectronic device, comprising:

a converter configured to convert a voltage of an electric energy into a predetermined voltage;

a capacitor configured to store an electric energy transferred from the converter; and a controller configured to measure an amount of electrical charge of the capacitor in a current time slot, predict an available current of a next time slot based on an output current of the converter and the measured amount of electrical charge of the capacitor in the current time slot, and determine a consumed current of a load system of the next time slot to match the predicted available current, wherein the controller is configured to preferentially allocate a portion of the determined consumed current to blocks in the load system except for a microcontroller unit (MCU) among the blocks in the load system and control an operating frequency of the MCU based on a remaining portion of the determined consumed current.

15. The device of claim 1, wherein an interval of the next time slot is determined based on the voltage ripple and the capacitance of the capacitor.

16. A processor-implemented power control method of a microelectronic device, the method comprising:

measuring an amount of electrical charge of a capacitor;

predicting an available current of a next time slot based on an output current of a converter and the measured amount of electrical charge of the capacitor, the capacitor configured to store an electric energy transferred from the converter in a current time slot; and determining a consumed current of a load system of the next time slot to match the predicted available current, wherein an impedance of the converter is adjusted to maximize the electric energy and a delay occurring when the determined consumed current of the load system is applied to the load system is determined based on a voltage ripple and a capacitance of the capacitor.

17. The method of claim 16, wherein the predicting of the available current comprises predicting the available current of the next time slot based on any one or any combination of any two or more of:
- a change in an amount of electrical charge stored in the capacitor from a previous time slot to the current time slot;
- a difference between the amount of electrical charge stored in the capacitor in the current time slot and a target amount of electrical charge to be stored in the capacitor; and
- a change in an amount of output current of the converter from the previous time slot to the current time slot.

18. The method of claim 16, further comprising:
determining, based on a voltage of the capacitor, the amount of electrical charge stored in the capacitor.

19. The method of claim 16, further comprising:
preferentially allocating a portion of the determined consumed current to blocks in the load system except for a microcontroller unit (MCU) among the blocks in the load system; and
controlling an operating frequency of the MCU based on a remaining portion of the determined consumed current.

* * * * *